United States Patent [19]

Birmingham et al.

[11] Patent Number: 4,879,241

[45] Date of Patent: Nov. 7, 1989

[54] TYLOSIN RESISTANCE-CONFERRING GENE, DESIGNATED TLRB, FOR USE IN STREPTOMYCES AND OTHER ORGANISMS

[75] Inventors: Virginia A. Birmingham, Carmel; Eugene T. Seno, Indianapolis, both of Ind.

[73] Assignee: Eli Lilly and Company, Indianapolis, Ind.

[21] Appl. No.: 871,051

[22] Filed: Jun. 5, 1986

[51] Int. Cl.[4] .............. C12N 1/20; C12N 15/00; C12N 1/00; C12P 21/00; C12P 11/34; C12R 1/465; C07H 15/12

[52] U.S. Cl. .............. 435/253.5; 435/68; 435/91; 435/172.1; 435/472.3; 435/320; 435/886; 536/27; 935/6; 935/29; 935/38; 935/56; 935/60; 935/75

[58] Field of Search .............. 435/68, 91, 172.3, 253, 435/320, 886, 896; 935/6, 29, 38, 56, 60, 75, 82

[56] References Cited

U.S. PATENT DOCUMENTS 4,680,265  7/1987  Birmingham et al. .......... 435/172.3

OTHER PUBLICATIONS

Barany et al., *J. Bacteriology*, 144 698, (1980).
Stonesifer et al., *Mol. Gen. Genet.*, 202 348, (1986).
Benveniste and Davies, 1973, Proc. Natl. Acad. Sci. USA, 70(8):2276-2280.
Thompson et al., 1980, Nature, 286:525-527.
Fujisawa and Weisblum, 1981, J. Bacteriol., 146(2):621-631.
Thompson et al., 1982, J. Bacteriol., 151(2):668-677.
Thompson et al., 1982, J. Bacteriol., 151(2):678-685.
Thompson et al., 1982, Gene, 20:51-62.
Murakami et al., 1983, J. Antibiotics, 36(10):1305-1311.
Tohyama et al., 1984, J. Antibiotics, 37(12):1736-1737.
Nakano et al., 1984, J. Bacteriol., 157(1):79-83.
Bibb et al., 1985, Mol. Gen. Genet., 199:26-36.
Ohnuki et al., 1985, J. Bacteriol., 161(3):1010-1016.
Distler et al., 1985, FEMS Microbiology Letters, 30:151-154.
Vara et al., 1985, Gene, 33:197-206.
Birmingham et al., 1984, Abstracts of the ASM Conference on Genetics and Molecular Biology of Industrial Microorganisms, Bloomington, IN, Abstract No. 220.

Primary Examiner—Thomas G. Wiseman
Assistant Examiner—Joan Ellis
Attorney, Agent, or Firm—Ron K. Levy; Leroy Whitaker

[57] ABSTRACT

The tlrB gene is a novel tylosin resistance-conferring gene isolated from *Streptomyces fradiae* and used to construct a number of cloning vectors for use in Streptomyces and related organisms. One such cloning vector, plasmid pSVB9, can be obtained in *S. lividans* under the accession number NRRL 18073. *S. lividans* is the preferred host when the tlrB gene is used to select tylosin-resistant Streptomyces transformants.

22 Claims, 12 Drawing Sheets

Restriction Site and Function Map of
Plasmid pSVB9
(10.7 kb)

Restriction Site and Function Map of
Plasmid pHJL315
(38.8 kb)

Restriction Site and Function Map of
Plasmid pSVB25
(8.7 kb)

Restriction Site and Function Map of
Plasmid pSFH62
(10.9 kb)

Restriction Site and Function Map of
Plasmid pSKC13
(11.1 kb)

Restriction Site and Function Map of
Plasmid pSFH60
(6.3 kb)

Restriction Site and Function Map of
Plasmid pSFH61
(9.4 kb)

Restriction Site and Function Map of
Plasmid pSVB36
(11.6 kb)

Restriction Site and Function Map of
Plasmid pSVB2
(10.55 kb)

Restriction Site and Function Map of Plasmid pIJ903 (25.8 kb)

Restriction Site and Function Map of
Plasmid pSVB40
(6.0 kb)

Restriction Site and Function Map of
Plasmid pSVB47
(29.15 kb)

TYLOSIN RESISTANCE-CONFERRING GENE, DESIGNATED TLRB, FOR USE IN STREPTOMYCES AND OTHER ORGANISMS

SUMMARY OF THE INVENTION

The present invention comprises a novel tylosin resistance-conferring gene, designated tlrB, recombinant DNA cloning vectors that comprise the novel gene, and transformants containing the tylosin resistance-conferring vectors. *Streptomyces fradiae* produces tylosin, used in veterinary medicine as an animal growth promotant and antibiotic. Tylosin is a macrolide antibiotic consisting of a 16-member cyclic lactone and three sugar residues. The antibiotic activity of tylosin, like other macrolides, is due to inhibition of protein synthesis by a mechanism that involves the binding of tylosin to the ribosome.

The present invention provides tylosin resistance-conferring cloning vectors for use in Streptomyces and other host cells. The development and exploitation of recombinant DNA technology in Streptomyces depends upon the availability of selectable genetic markers on suitable cloning vectors. This development has been somewhat retarded by the low number of selectable markers presently available for use in Streptomyces. The present invention is useful and especially important in that it expands the number of selectable markers suitable for such use.

The vectors of the present method are particularly useful, because the vectors ar small, versatile, and can be transformed and selected in a variety of tylosin-sensitive Streptomyces cells. Streptomyces provides over half of the clinically important antibiotics and thus is a commercially significant group. The present invention provides new and useful cloning systems and vectors for this industrially important group and allows for the cloning of genes both for increasing the yields of known antibiotics and also for producing new antibiotics and antibiotic derivatives.

The present invention further provides vectors that enable selection of Streptomyces transformants from a background of untransformed cells. After the addition of non-selectable DNA to a vector of the present invention, the modified vector can be transformed into Streptomyces and transformants selected by their tylosin-resistant phenotype. Because transformation is a relatively low frequency event, such a functional test is a practical necessity for determining which cell(s), of among the millions of cells, has acquired the transforming DNA.

For purposes of the present invention, as disclosed and claimed herein, the following terms are defined below.

ApR—the ampicillin-resistant phenotype or gene conferring same.

mel—the tyrosinase gene.

Phasmid—a recombinant DNA vector that may act as a phage or as a plasmid.

Recombinant DNA Cloning Vector— any autonomously replicating or integrating agent, including, but not limited to, plasmids, comprising a DNA molecule to which one or more additional DNA segments can be or have been added.

Restriction Fragment— any linear DNA molecule generated by the action of one or more restriction enzymes.

Sensitive Host Cell— a host cell that cannot grow in the presence of a given antibiotic without a DNA segment that provides resistance thereto.

TcR— the tetracycline-resistant phenotype or gene conferring same.

tlrA— a tylosin resistance-conferring gene of type A.

tlrB— a tylosin resistance-conferring gene of type B.

Transformant— a recipient host cell that has undergone transformation.

Transformation— the introduction of DNA into a recipient host cell that changes the genotype and results in a change in the recipient cell.

tsrR— the thiostrepton-resistant phenotype or gene conferring same.

tyl— a tylosin biosynthetic gene.

BRIEF DESCRIPTION OF THE FIGURES

The figures described below are drawn to scale. For some restriction enzymes, such as SauIIIA1, only the significant cut sites are shown.

DETAILED DESCRIPTION OF THE INVENTION

Figure 1:
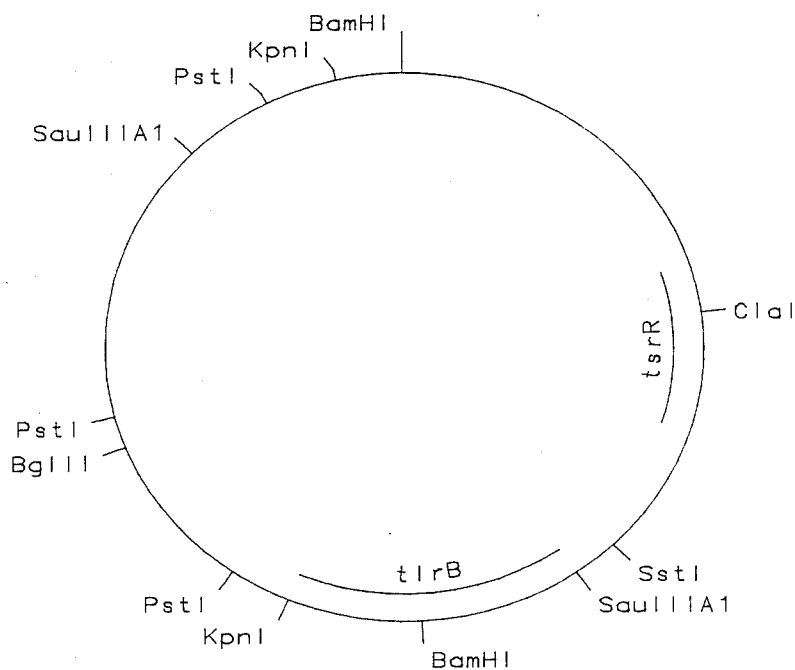
FIG. 1 is a restriction site and function map of plasmid pSVB9.
Figure 2:
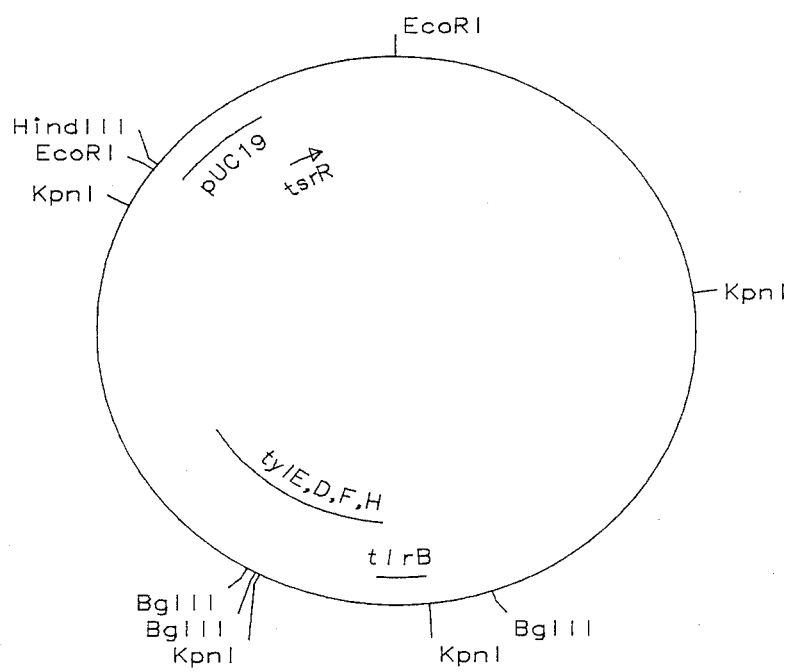
FIG. 2 is a restriction site and function map of plasmid pHJL315.

The present invention concerns a novel tylosin resistance-conferring gene, designated tlrB, that is useful as a selectable marker in many organisms. The tlrB gene can be isolated from plasmid pSVB9 on an ~3.35 kb BglII-SstI restriction fragment; plasmid pSVB9 can be isolated from *Streptomyces lividans* TK23/pSVB9, a strain deposited and made part of the permanent culture collection of the Agricultural Research Service, Northern Regional Research Center (NRRL), Peoria, Il. 61604, under the accession number NRRL 18073. A restriction site and function map of plasmid pSVB9 is presented in FIG. 1 of the accompanying drawings. Plasmid pSVB9 can be isolated from *S. lividans* TK23/pSVB9 in substantial accordance with the procedure described in Example 1. The tlrB gene can also be isolated from plasmid pHJL315, a plasmid available from the NRRL under the accession number NRRL B-18047. A restriction site and function map of plasmid pHJL315 is presented in FIG. 2 of the accompanying drawings.

Figure 3:
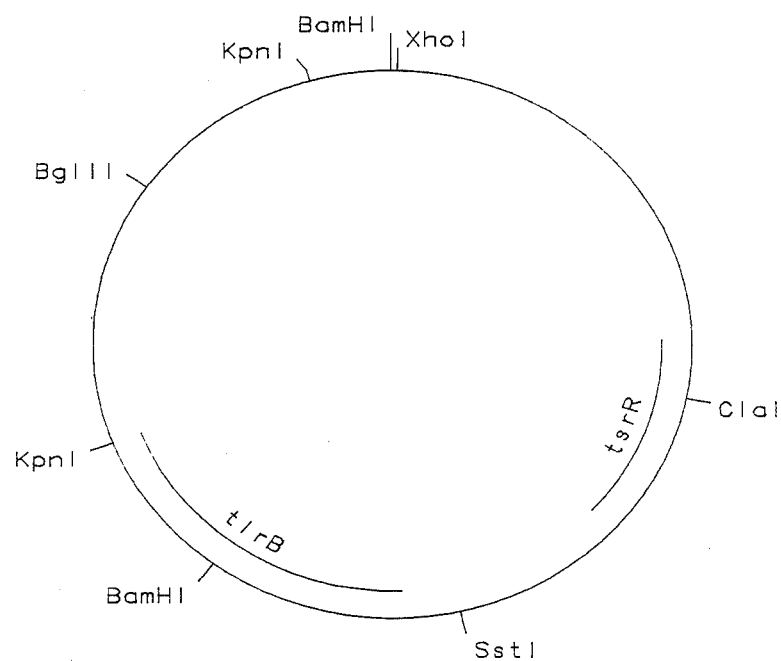
FIG. 3 is a restriction site and function map of plasmid pSVB25.

Plasmids pSVB9 and pHJL315 serve as useful starting material for the construction of other vectors that confer tlrB-mediated tylosin resistance. For example, the ~3.35 kb BglII-SstI, tylosin resistance-conferring restriction fragment of plasmid pSVB9 was isolated and inserted into the large BglII-SstI restriction fragment of plasmid pIJ702 (ATCC 39155) to yield plasmid pSVB25. Plasmid pSVB25 comprises the tlrB gene and confers tylosin resistance to a variety of organisms, as more fully described below. The construction protocol for plasmid pSVB25 is given in Example 2; a restriction site and function map of plasmid pSVB25 is presented in FIG. 3 of the accompanying drawings.

Figure 4:
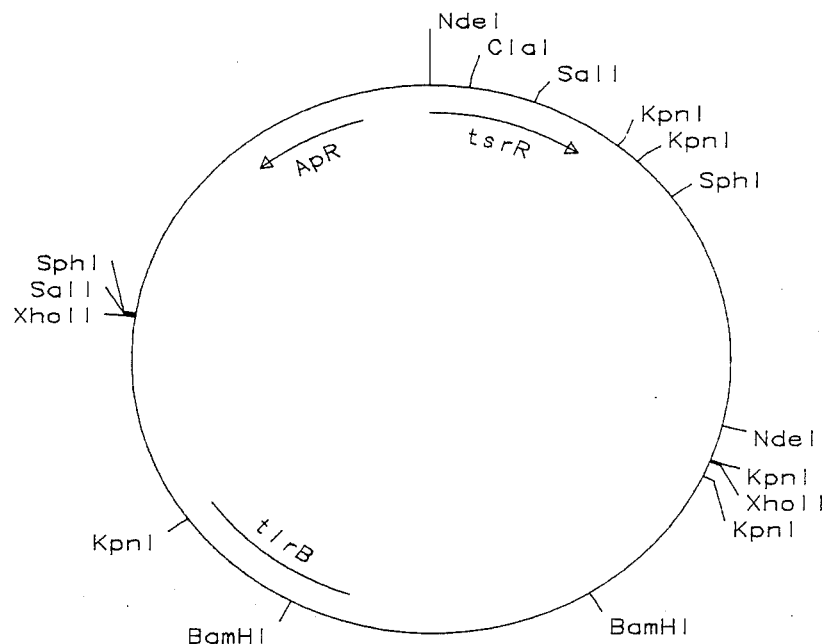
FIG. 4 is a restriction site and function map of plasmid pSFH62.
Figure 5:
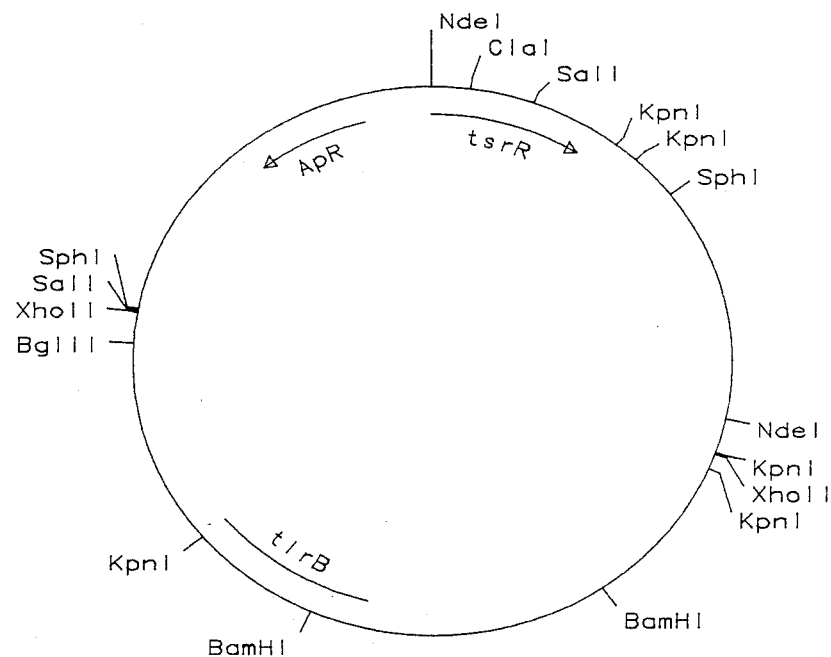
FIG. 5 is a restriction site and function map of plasmid pSKC13.

Plasmid pHJL315 serves as useful starting material for a variety of vectors of the present invention that contain the tlrB gene. Plasmid pHJL315 was digested with restriction enzyme BglII, and the resulting ~5.0 kb BglII restriction fragment that comprises the tlrB gene was inserted into BamHI-digested plasmid pHJL401 to yield plasmids pSFH62 and pSFH63. Plasmid pHJL401 is disclosed in U.S. patent application Ser. No. 841,920, filed 3-20-86, which is a continuation-in-part of Ser. No. 763,172, filed 8-7-85, Plasmids pSFH62 and pSFH63 differ only with respect to the orientation of the ~5.0 kb BglII restriction fragment; a restriction site and function map of plasmid pSFH62 is presented in FIG. 4 of the accompanying drawings. In a similar construction, an ~0.2 kb BglII restriction fragment adjacent to the ~5.0 kb, tlrB-containing BglII restriction fragment on plasmid pHJL315 was inserted along with the ~5.0 kb fragment, yielding a total insert size of ~5.2 kb, into BamHI-digested plasmid pHJL401 to yield plasmid pSKC13. A restriction site and function map of plasmid pSKC13 is presented in FIG. 5 of the accompanying drawings. The construction protocol for plasmids pSFH62, pSFH63, and pSKC13 is presented in Example 3.

Figure 6:
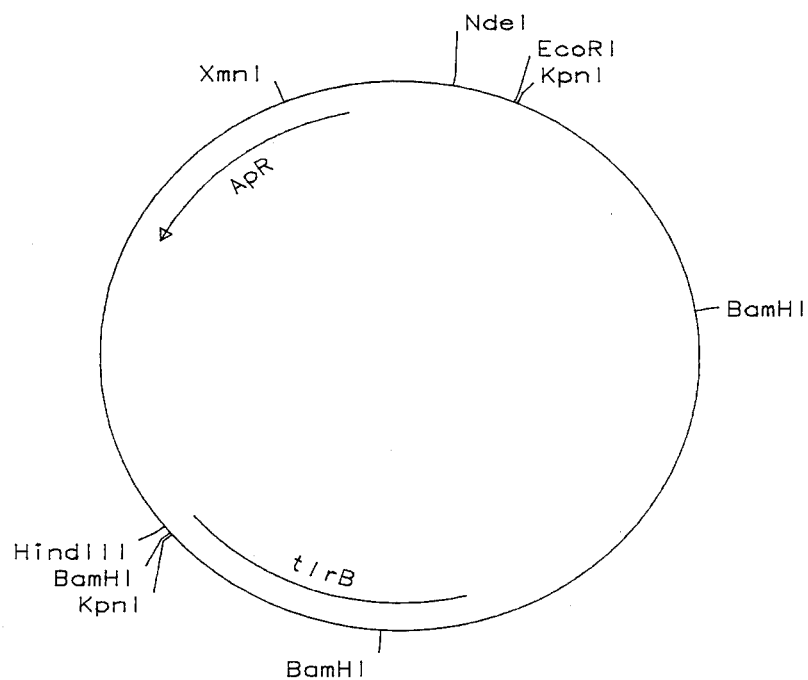
FIG. 6 is a restriction site and function map of plasmid pSFH60.
Figure 7:
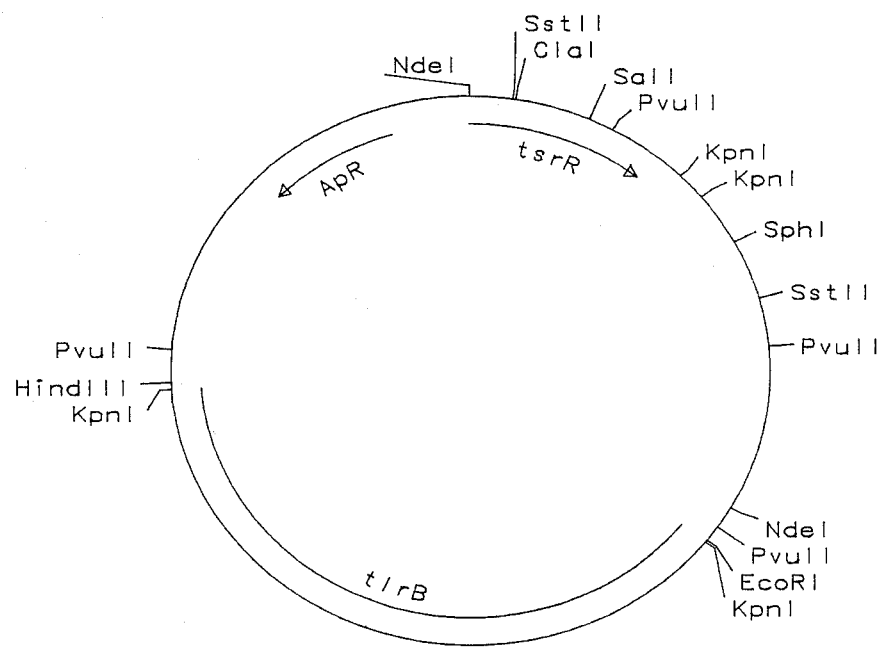
FIG. 7 is a restriction site and function map of plasmid pSFH61.

Plasmid pSKC13 was digested with restriction enzyme KpnI, and the ~b 3.8 kb, tlrB-containing KpnI restriction fragment was isolated and inserted into KpnI-digested plasmid pUC19 (ATCC 37254) to yield plasmids pSFH60 and pSFH60.1. The two plasmids differ only with respect to the orientation of the ~3.8 kb KpnI fragment; a restriction site and function map of plasmid pSFH60 is presented in FIG. 6 of the accompanying drawings. The ~3.8 kb, tlrB-containing EcoRI-HindIII restriction fragment of plasmid pSFH60 was isolated and then inserted into EcoRI-HindIII-digested plasmid pHJL401 to yield plasmid pSFH61. A restriction site and function map of plasmid pSFH61 is presented in FIG. 7 of the accompanying drawings. The construction protocol for plasmids pSFH60, pSFH60.1, and pSFH61 is described in Example 4.

Figure 8:
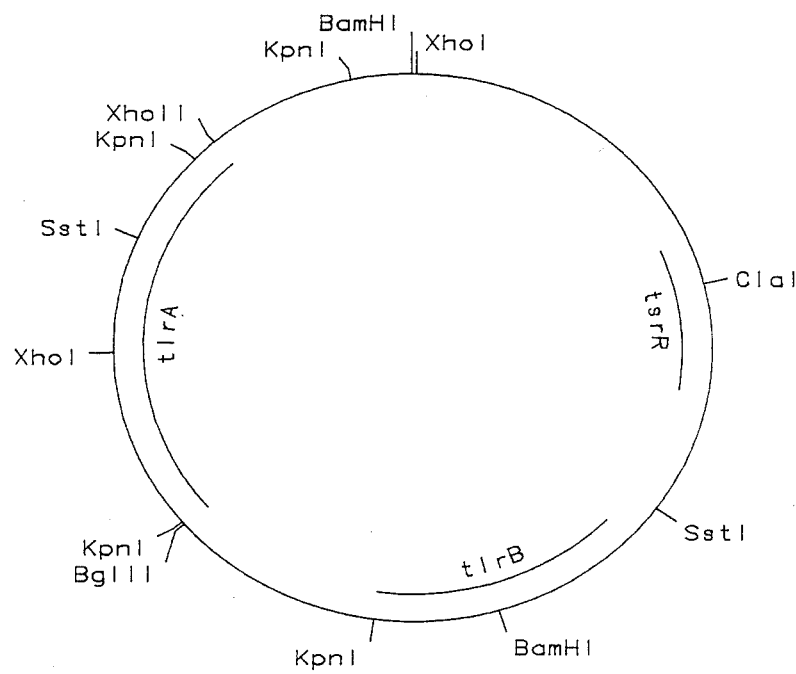
FIG. 8 is a restriction site and function map of plasmid pSVB36.

The plasmids of the present invention can be readily modified by the addition of other DNA to make even more useful vectors. To illustrate, the tlrA gene, which confers tylosin resistance and is described in U.S. patent application Ser. No. 653 975, filed 9-25-84, now issued as U.S. Pat. No. 4,680,265 (July 14, 1987 ) has been added to plasmid pSVB25 to yield plasmids pSVB36 and pSVB37. Plasmids pSVB36 and pSVB37 were constructed by inserting the ~2.86 kb, tlrA gene-containing BamHI-BglII restriction fragment of plasmid pSVB2 (deposited in Streptomyces lividans TK23 under accession number NRRL 15880) into BglII-digested plasmid pSVB25. The two plasmids differ only with respect to the orientation of the ~2.86 kb restriction fragment, and a restriction site and function map of plasmid pSVB36 is presented in FIG. 8 of the accompanying drawings. The construction protocol for plasmids pSVB36 and pSVB37 is presented in Example 5.

Figure 11:
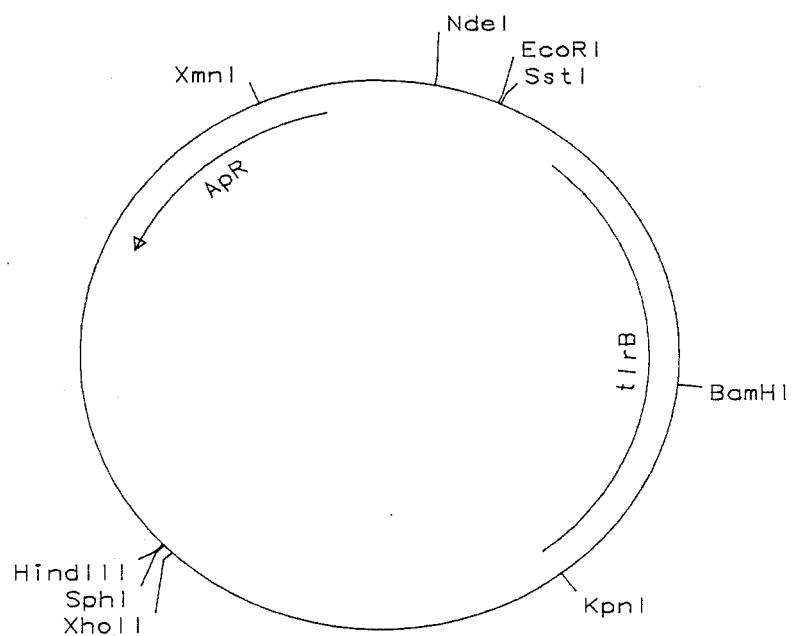
FIG. 11 is a restriction site and function map of plasmid pSVB40.
Figure 12:
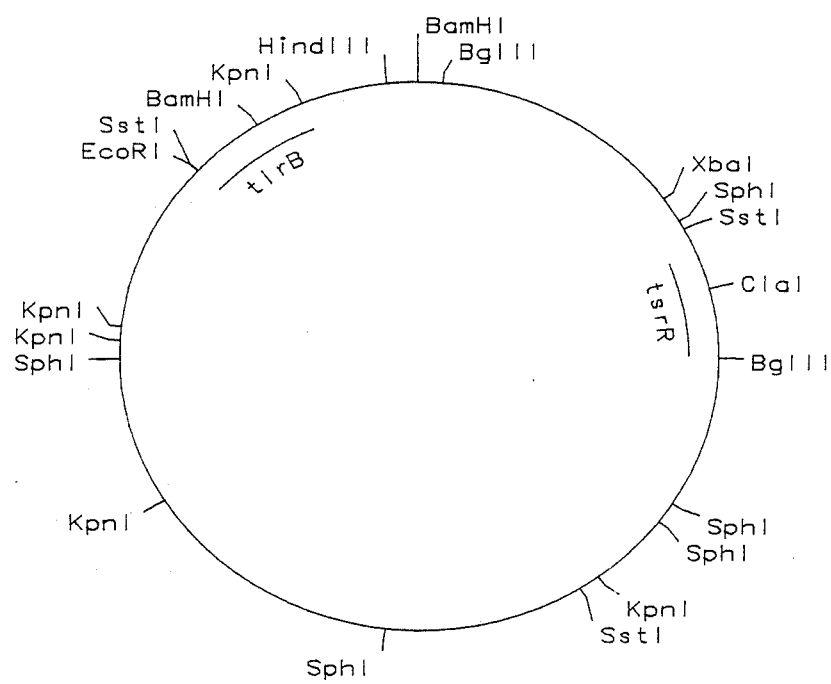
FIG. 12 is a restriction site and function map of plasmid pSVB47.

The tlrB gene has also been used to construct vectors that have a low copy number in Streptomyces. The ~3.35 kb, tlrB-containing SstI-BglII restriction fragment of plasmid pSVB25 was inserted into SstI-BamHI-digested plasmid pUC19 to yield plasmid pSVB40. Plasmid pSVB40 was then digested with restriction enzymes EcoRI and HindIII, and the ~3.8 kb, tlrB-containing EcoRI-Hind III restriction fragment was isolated, purified, and ligated to EcoRI-HindIII-digested plasmid pIJ903 to yield plasmid pSVB47. Plasmid pIJ903 was disclosed in Lydiate et al., 1985, Gene 35:223-235, and can be obtained from the John Innes Streptomyces Culture Collection, John Innes Institute, Colney Lane, Norwich, England NR4-7UH, under the accession number 3417. Plasmid pIJ903 has a copy number of about 1 in Streptomyces; plasmid pSVB47 has a similar copy number. Restriction site and function maps of plasmids pSVB40 and pSVB47 are respectively presented in FIGS. 11 and 12. The construction protocol for plasmid pSVB47 is presented in Example 7.

Restriction fragments used to construct vectors illustrative of the present invention can be conventionally modified to facilitate ligation. For example, molecular linkers can be provided to a particular tylosin resistance gene-containing restriction fragment or to DNA comprising vector replication or integration functions. Thus, specific sites for subsequent ligation can be conveniently constructed. In addition, the various tylosin resistance gene-containing restriction fragments, origin of replication, or integration sequences of a given vector can be modified by adding, eliminating, or substituting certain nucleotides to alter characteristics and to provide a variety of restriction sites for ligation of DNA. Those skilled in the art understand nucleotide chemistry and the genetic code and thus which nucleotides are interchangeable and which DNA modifications are desirable for a specific purpose. It is also noteworthy that a given tylosin resistance gene-containing restriction fragment is not limited to a particular position on a cloning vector, as long as critical, vector-controlled functions are not disrupted. Those skilled in the art understand or can readily determine which sites on a vector are advantageous for the ligation or insertion of a particular tylosin resistance gene-containing restriction fragment.

The tlrB gene was isolated from a tylosin producing strain of *Streptomyces fradiae*. Thus, genomic DNA of *S. fradiae* was partially digested with restriction enzyme SauIIIAl, and the resulting DNA was inserted into BglII-digested plasmid pIJ702 to yield a number of tlrB-containing plasmids, including plasmid pSVB9. In a similar fashion, genomic DNA from the same strain of *S. fradiae* was partially digested with restriction enzyme MboI, and the resulting MboI-digested DNA was cloned into the BamHI site of plasmid pKC462A, a plasmid available from the NRRL under the accession number NRRL B-15973. The insert was excised on an EcoRI restriction fragment and cloned into plasmid pHJL401 to yield plasmid pHJL315. Because the tlrB gene was isolated from *S. fradiae*, the tlrB gene functions in *S. fradiae*, but the unmodified gene also functions in other organisms.

The vectors of the present invention have also been used to transform *Streptomyces lividans* to tylosin resistance, as described in Example 6. Thus, the tlrB gene can be used to transform a variety of Streptomyces strains to tylosin resistance. However, the tlrB gene does not confer high-level tylosin resistance to *S. griseofuscus*, thus indicating that the promoter of the tlrB gene may not efficiently function in all host cells.

However, plasmids pSVB9 and pHJL315 contain the complete tlrB gene: (1) a promoter that directs transcription of the protein-coding sequence; (2) a sequence that, when transcribed into mRNA, directs translation of the transcript; (3) a protein-coding sequence; and (4) a transcription terminator. Each of these elements is independently useful and can, through the techniques of recombinant DNA technology, be used to form recombinant genes of great variety. DNA sequencing of the ~3.35 kb BglII-SstI restriction fragment of plasmid pSVB9 will reveal the precise location of the tlrB coding sequence and thus allow one to position other promoters in reading phase with the tlrB coding sequence. By choosing the proper promoter, one can construct vectors that drive expression of the tlrB gene product in any given host cell. The promoter of the tlrB gene is useful in its own right. The promoter and other regulatory elements of the tlrB gene can be linked to the coding sequence of a non-tylosin antibiotic biosynthetic gene to prepare a hybrid gene that might function in *Streptomyces fradiae* to yield a hybrid antibiotic. Thus, the individual elements of the gene on the plasmids described herein comprise important components of the present invention.

Although the above-described vectors comprise the Streptomyces replicon derived either from plasmid pIJ702, pIJ903, or pHJL401, a variety of known Streptomyces replicons can be used to construct equally useful vectors with different host ranges. Table 1 is an illustrative, but not comprehensive, listing of Streptomyces plasmids from which Streptomyces replicons can be obtained. Those skilled in the art recognize that, so long as the replicon function is not disrupted, all or part of the plasmids may be used to construct vectors that contain the tlrB gene of the present invention. The plasmid-containing host and depository accession number are also listed in Table 1.

TABLE 1

| Streptomyces Plasmids | | |
|---|---|---|
| Plasmid | Host | Accession Number |
| SCP2 | *Streptomyces coelicolor* A3(2) | NRRL 15042 |
| SCP2* | *Streptomyces coelicolor* M110 | NRRL 15041 |
| pEL7 | *Streptomyces ambofaciens*/pEL7 | NRRL 12523 |
| pUC6 | *Streptomyces espinosus* | NRRL 11439 |
| pUC3 | *Streptomyces* 3022A | NRRL 11441 |
| SLP1 | *Streptomyces lividans* | NCIB* 11417 |
| pNM100 | *Streptomyces virginiae* | NRRL 15156 |
| pEL103 | *Streptomyces granuloruber* A399 12.13/pEL103 | NRRL 12549 |
| pIJ702 | *Streptomyces lividans* | ATCC** 39155 |

*National Collection of Industrial Bacteria (NCIB), Torry Research Station, Post Office Box 31, 135 Abbey Road, Aberdeen AB98DG, Scotland, United Kingdom.
**American Type Culture Collection, Rockville, MD 20852.

Of course, the tlrB gene can be used to construct vectors other than plasmids. Phage φC31 is a well-known Streptomyces phage that is an excellent source of starting material for constructing integrative tylosin resistance-conferring vectors that further exemplify the present invention. A derivative of phage φC31, phasmid pKC331, is especially preferred for constructing such integrating vectors and can be obtained from *E. coli* K12 BE447/pKC331 (NRRL B-15828). φC31-type phages are integrative vectors and can be readily modified to incorporate the tlrB gene and thus confer tylosin resistance to Streptomyces.

The vectors of the present invention comprise a Streptomyces replicon and a tylosin resistance-conferring restriction fragment. Because amplification and manipulation of plasmids is done faster and more efficiently in *E. coli* than in Streptomyces, it is convenient to add DNA sequences that also allow for replication in *E. coli*. Thus, the addition of functional replicon-containing and antibiotic resistance-conferring restriction fragments from *E. coli* plasmids such as, for example, pBR322, pACYC184, pBR325, pBR328, and the like is highly advantageous and adds to the general utility of the present illustrative vectors.

The vectors used in the present method confer tylosin resistance to tylosin-sensitive Streptomyces or related host cells. Although 10 μg/ml of tylosin is generally toxic to tylosin-sensitive Streptomyces, vectors of the present invention confer resistance to levels approaching 10 mg/ml of tylosin. The preferred tylosin concentration for purposes of selection, however, is about 500 μg/ml for *Streptomyces lividans*. The preferred tylosin concentration for purposes of selection for other tylosin-sensitive microorganisms is readily determined by procedures well-known in the art and depends upon the promoter used to drive expression of the tlrB gene and the organism's sensitivity to tylosin.

The tlrB gene confers resistance to tylosin and may confer resistance to other antibiotics. Inducible resistance to macrolide antibiotics, such as tylosin and erythromycin in Gram-positive bacteria (such as Staphylococcus, Streptomyces, Streptococcus, and Bacillus), is associated with co-resistance to lincosamide and streptogramin-type B antibiotics; this multi-drug resistant phenotype is called the MLS-resistant phenotype (Fujisawa and Weisblum, 1981, J. Bacteriol. 146:621-631). In *Staphylococcus aureus*, the MLS-resistant phenotype arises upon specific methylation of an adenine residue in 23S ribosomal RNA (rRNA) resulting in the formation of $N^6$-dimethyladenine. A number of Streptomyces species, most of which produce MLS-antibiotics, express the MLS-resistant phenotype. The rRNA from these species contains $N^6$-monomethyladenine, $N^6$-dimethyladenine, or both. MLS-resistance in *Streptomyces erythreus*, an erythromycin producer, arises upon $N^6$-dimethylation of a single adenine residue in 23S rRNA. Thompson et al. cloned a *S. erythreus* gene that conferred erythromycin resistance in *S. lividans* via a mechanism that generated $N^6$-dimethyladenine in 23S rRNA. It is highly likely and expected that the tlrB gene confers the MLS-resistant phenotype.

*Streptomyces lividans* TK23 is sensitive to tylosin at the concentrations (~500 μg/ml) used for selection of transformants containing the tlrB gene. The TK23 strain does seem to possess an endogenous MLS-resistance-conferring capability, however. In preliminary experiments, TK23 was sensitive to low levels (≦25 μg/ml) of tylosin, but pre-exposure to 1 μg/ml of tylosin induced resistance to tylosin at concentrations up to 100 μg/ml. The endogenous MLS system, however, is apparently incapable of conferring resistance to tylosin at levels used to select the cloned tlrB gene.

The recombinant DNA cloning vectors of the present invention have broad utility and help fill the need for suitable cloning vehicles for use in Streptomyces and related organisms. Moreover, the ability of the present vectors to confer tylosin resistance provides a functional means for selecting transformants. This is important because of the practical necessity for determining and selecting the particular cells that have acquired vector DNA in a transformation procedure.

Additional DNA segments, that lack functional tests for their presence, can also be inserted into the present vectors, and transformants containing the non-selectable DNA can be isolated by selection for tylosin resistance. Such non-selectable DNA segments can be inserted at any site, except within regions necessary for plasmid function and replication or within the tlrB gene, and include, but are not limited to, genes that specify antibiotic modification enzymes and regulatory genes of all types.

More particularly, a non-selectable DNA segment that comprises a gene is inserted into a plasmid such as, for example, plasmid pSVB9 at the central ClaI restriction site of the thiostrepton resistance gene. Such an insertion inactivates the thiostrepton resistance gene and thus allows for the easy identification of transformants containing the recombinant plasmid. This is done by first selecting for tylosin resistance and, secondarily, identifying those tylosin-resistant transformants that are not resistant to thiostrepton. Therefore, the ability to select for tylosin resistance in Streptomyces and related cells allows for the efficient isolation of the extremely rare cells that contain the particular non-selectable DNA of interest.

The functional test for tylosin resistance, described above, is also used to locate DNA segments that act as control elements and direct expression of an individual antibiotic resistance gene. Such segments, including, but not limited to, promoters, attenuators, repressors, inducers, ribosome-binding sites, and the like, are used to control the expression of other genes in Streptomyces and related organisms.

The tylosin resistance-conferring vectors of the present invention are also useful for ensuring that linked DNA segments are stably maintained in host cells over many generations. These genes or DNA fragments, covalently linked to the tylosin resistance-conferring DNA and propagated in Streptomyces, are maintained by exposing the transformants to levels of tylosin toxic to non-transformed cells. Therefore, transformants that lose the vector, and consequently lose any covalently linked DNA, cannot grow and are eliminated from the culture. Thus, the vectors of the present invention can stabilize and maintain any DNA sequence of interest.

The cloning vectors and transformants of the present invention provide for the cloning of genes to improve yields of various products that are currently produced in Streptomyces and related cells. Examples of such products include, but are not limited to, Streptomycin, Tylosin, Cephalosporins, Actaplanin, Narasin, Monensin, Tobramycin, Erythromycin, and the like. The present invention also provides selectable vectors that are useful for cloning, characterizing, and reconstructing DNA sequences that code for: commercially important proteins such as, for example, human insulin, human proinsulin, glucagon, interferon and the like; enzymatic functions in metabolic pathways leading to commercially important processes and compounds; or control elements that improve gene expression. These desired DNA sequences also include, but are not limited to, DNA that codes for enzymes that catalyze synthesis of derivatized antibiotics such as, for example, Streptomycin, Cephalosporin, Tylosin, Actaplanin, Narasin, Monensin and Erythromycin derivatives, or for enzymes that mediate and increase bioproduction of antibiotics or other products. The capability for isolating and using such DNA segments allows for increasing the yield and availability of antibiotics that are produced by Streptomyces and related organisms.

Streptomyces can be cultured in a number of ways using any of several different media. Preferred carbohydrate sources in a culture medium include, for example, molasses, glucose, dextrin, and glycerol. Nitrogen sources include, for example, soy flour, amino acid mixtures, and peptones. Nutrient inorganic salts are also incorporated and include the customary salts capable of yielding sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium.

Streptomyces is grown under aerobic culture conditions over a relatively wide pH range of about 5 to 9 at temperatures ranging from about 15° to 40° C. For plasmid stability and maintenance, it is desirable to start with a culture medium at a pH of about 7.2 and maintain a culture temperature of about 30° C.

The following examples further illustrate and describe the invention disclosed herein. The invention is not limited in scope by reason of any of the following Examples; sources of reagents or equipment are provided merely for convenience and in no way limit the invention. Both an explanation of and the actual procedures for constructing the invention are described where appropriate.

EXAMPLE 1

Isolation of Plasmid pSVB9

A. Culture of *Streptomyces lividans* TK23/pSVB9

About $10^8$ spores of *Streptomyces lividans* TK23/pSVB9 (NRRL 18073) were inoculated into 10 ml of TSB medium (Trypticase Soy Broth*) containing 10 μg/ml thiostrepton and grown at 29° C. until the culture was in early stationary phase. The culture was then homogenized, and 5 ml of the homogenized culture were used to inoculate 100 ml of TSB also containing thiostrepton. The 100 ml of culture were incubated at 29° C. until the *Streptomyces lividans* TK23/pSVB9 cells reached stationary phase.

*TSB is made at 30 g/l and is obtained from: Bethesda Research Laboratories (BRL), Inc., 8717 Grovemont Circle, P.O. Box 577, Gaithersburg, Md. 20760.

B. Plasmid Isolation

The cells were collected and washed once with a 10.3% sucrose solution. The cells were then suspended in 24 ml of 10.3% sucrose, and 6 ml of 5X lysozyme solution (125 mM Tris-HCl, pH=8; 125 mM Na$_2$EDTA, pH=8; 10 mg/ml lysozyme; and 10.3% sucrose) were added. The solution was mixed and then incubated at 30° C. for 30–60 minutes, and then, about 18 ml of a solution that was 0.3 M NaOH, 1% SDS, and prewarmed to 50° C. were added, mixed and the resulting mixture incubated at 80° C. for 10 minutes. The mixture was then cooled to room temperature, and 12 ml of a solution made by mixing 500 g phenol, 500 g CHCl$_3$, and 0.5 g 8-hydroxyquinoline in 200 ml H$_2$O were added and mixed well with the cell-extract. The phases were separated by centrifugation at 6000–8000 rpm for 10 minutes; approximately 45 ml of the resulting upper phase were transferred to a clean bottle.

Next, 4.5 ml of 3 M NaOAc and 50 ml of isopropanol were added to the supernatant, and the solution was mixed and left at room temperature for 30 minutes. The solution was then centrifuged (8000 rpm for 30 minutes) and the resulting supernatant discarded. The pellet was resuspended in 7.5 ml TE buffer (10 mM Tris-HCl, pH=8, and 1 mM EDTA) containing 8 g of CsCl. About 0.5 ml of a 10 mg/ml solution of ethidium bromide was added to the solution, which was then centrifuged at 40,000 rpm for 48 hours at 20° C. The fraction containing the plasmid band was extracted 3-5 times with isopropanol saturated with TE buffer and CsCl to remove the ethidium bromide. After the extractions, the sample was diluted with four volumes of TE buffer, and then, two-and-one-half volumes of ethanol were added. The resulting solution was mixed and incubated overnight at $-20°$ C.

The precipitate resulting from the overnight incubation at $-20°$ C. was collected by centrifugation (10,000 rpm for 30 minutes), dried, and reprecipitated twice. The precipitations were done by suspending the pellet in TE buffer, adding NaOAc to 0.3 M, adding 2.5 volumes ethanol, chilling at $-70°$ C. for 10-15 minutes, and then centrifuging the solution as above. The procedure yields about 100 µg of plasmid pSVB9 DNA, which was suspended in TE buffer at a concentration of 1 µg/µl and stored at 4° C.

EXAMPLE 2

Construction of Plasmid pSVB 25

*Streptomyces lividans*/pIJ702 (ATCC 39155) was cultured and plasmid pIJ702 isolated in substantial accordance with the teaching of Example 1. Thiostrepton selection (10 µg/ml) was used to ensure plasmid pIJ702 maintenance. The ~100 µg of plasmid pIJ702 DNA obtained were suspended in 1 ml of TE and stored at 4° C.

About 500 ng (5 µl) of plasmid pIJ702 DNA were added to 2 µl of 10X SacI buffer (60 mM Tris-HCl, pH=7.4; 60 mM MgCl$_2$; 60 mM 2-mercaptoethanol; and 1 mg/ml bovine serum albumin (BSA)), 12 µl of H$_2$O and 1.5 µl (~15 units; unit definitions herein correspond to those of New England Biolabs, 32 Tozer Road, Beverly, Mass. 01915-9990, unless otherwise indicated) of restriction enzyme SacI, an isoschizomer of restriction enzyme SstI. The resulting reaction was incubated at 37° C. for one hour, when about 3 µl of the reaction mixture were removed and subjected to agarose gel electrophoresis to determine completeness of digestion. About 4 µl of 10X BglII buffer (1.0 M NaCl; 100 mM Tris-HCl, pH=7.4; 100 mM MgCl$_2$; 100 mM 2-mercaptoethanol; and 1 mg/ml BSA), 16µl of H$_2$O, and 2 µl (~16 units) of restriction enzyme BglII were added to the solution of SacI-digested plasmid pIJ702 DNA, and the resulting reaction was incubated at 37° C. for 1 hour. About 6 µl of the reaction mixture were removed to check completeness of digestion. Then, the SacI-BglII-digested DNA was collected by adjusting the sodium acetate (NaOAc) concentration of the reaction mixture to 0.30 M, adding two volumes of ethanol, chilling the reaction mixture to $-70°$ C., and centrifuging to pellet the precipitated DNA. The pellet of BglII-SacI-digested plasmid pIJ702 DNA was resuspended in 100 µl of 50 mM Tris-HCl, pH=8.0. About 1 µl of a 1:100 dilution calf-intestinal alkaline phosphatase (Boehringer-Mannheim) in 50 mM Tris-HCl, pH=8, was added to the solution of DNA, and the resulting reaction was incubated at 37° C. for 30 minutes. The reaction was terminated by incubating the reaction mixture at 70° C. for one hour.

About 625 ng of plasmid pSVB9 DNA in 25 µl of TE buffer were added to 6 µl of 10X SacI buffer, 26 µl of H$_2$O, and 2 µl (~20 units) of restriction enzyme SacI, and the resulting reaction was incubated at 37° C. for one hour. About 3 µl of 1 M NaCl and 2 µl of restriction enzyme ClaI were then added to the reaction mixture, which was incubated at 37° C. for another hour. The ClaI-digestion lowers the frequency of undesired ligation products during the ligation to construct plasmid pSVB25. About 8 µl of the reaction mixture were subjected to agarose gel electrophoresis to check completeness of the digestions, and 1 µl of 1 M NaCl and 1 µl (~8 units) of restriction enzyme BglII were added to the remaining solution of ClaI-SacI-digested DNA; the reaction mixture was incubated for another hour at 37° C. About 8 µl of the reaction mixture were removed to check the completeness of the BglII digestion.

About 77 µl of the BglII-SacI-digested, alkaline phosphatase-treated plasmid pIJ702 DNA were added to 32 µl of the BglII-SacI-ClaI-digested plasmid pSVB9 DNA, 11 µl of 3 M sodium acetate (NaOAc), and 300 µl of absolute ethanol. The solution was mixed, chilled at $-70°$ C. for 30 minutes, and then centrifuged to pellet the DNA. The DNA was resuspended in 12 µl of 1X ligase buffer (50 mM Tris-HCl, pH=7.8; 10 mM MgCl$_2$; 20 mM dithiothreitol (DTT); 1.0 mM ATP; and 50 µg/ml BSA). About 1 µl (~1 unit, Boehringer-Mannheim) of T4 DNA ligase was added to the solution of DNA, and the resulting reaction was incubated at 15° C. overnight (~16 hours). The ligated DNA constituted the desired plasmid pSVB25 DNA. A restriction site and function map of plasmid pSVB25 is presented in FIG. 3 of the accompanying drawings. The ligated DNA was used to transform *Streptomyces lividans* TK23 as described in Example 6, below. *S. lividans* TK23/pIJ702 transformants were distinguished from *S. lividans* TK23/pSVB25 transformants by the color of the colonies on the transformation plates. Plasmid pIJ702 carries an intact tyrosinase gene; thus *S. lividans* TK23/pIJ702 transformants are black on tyrosine-containing plates. The tyrosinase gene is inactivated during the construction of plasmid pSVB25; consequently, *S. lividans* TK23/pSVB25 transformants are not black on tyrosine-containing plates.

EXAMPLE 3

Construction of Plasmids pSFH62, pSFH63, and pSKC13

Plasmid DNA was obtained from *E. coli* K12 HB101/pHJL315 to use in the construction of plasmids pSFH62, pSFH63, and pSKC13 in accordance with the following procedure, which is adapted from Maniatis et al., 1982, *Molecular Cloning* (Cold Spring Harbor Laboratory). This same procedure was used, but on a smaller scale and with the ultra centrifugation steps replaced with phenol followed by chloroform extractions, to prepare the plasmid DNA used to identify the various *E. coli* transformants of the present invention.

About 500 ml of stationary-phase *E. coli* K12 JM109/pHJL315 cells are harvested by centrifugation at 4000Xg for 10 minutes at 4° C., and the supernatant is discarded. The cell pellet is washed in 100 ml of ice-cold STE buffer (0.1 M NaCl; 10 mM Tris-HCl, pH 7.8; and 1 mM EDTA). After the cell pellet is washed, the pellet is resuspended in 10 ml of Solution 1 (50 mM glucose; 25 mM Tris-HCl, pH=8.0; and 10 mM EDTA) that contains 5 mg/ml lysozyme and is left at room temperature for 10 minutes. Twenty ml of Solution 2 (0.2 N NaOH and 1% SDS) are then added to the lysozyme-treated cells, and the solution is gently mixed by inversion. The mixture is incubated on ice for 10 minutes.

Fifteen ml of ice-cold, 5 M potassium acetate, pH=4.8, are added to the lysed-cell mixture, and the solution is mixed by inversion. The solution is incubated on ice for 10 minutes. The 5 M potassium acetate solution is prepared by adding 11.5 ml of glacial acetic acid to 28.5 ml of water and 60 ml of 5 M potassium acetate; the resulting solution is 3 M with respect to potassium and 5 M with respect to acetate.

The lysed cell mixture is centrifuged in a Beckman SW27 rotor (or its equivalent) at 20,000 rpm for 20 minutes at 4° C. The cell DNA and debris forms a pellet on the bottom of the tube. About 36 ml of supernatant are recovered, and 0.6 volumes of isopropanol are added, mixed, and the resulting solution left at room temperature for 15 minutes. The plasmid DNA is collected by centrifugation at 12,000Xg for 30 minutes at room temperature. The supernatant is discarded, and the DNA pellet is washed with 70% ethanol at room temperature. The ethanol wash is decanted, and the pellet is dried in a vacuum desiccator. The pellet is then resuspended in 8 ml of TE buffer.

Eight grams of CsCl are added to the DNA solution. About 0.8 ml of a 10 mg/ml solution of ethidium bromide in water are added for each 10 ml of CsCl-DNA solution. The final density of the solution is about 1.55 g/ml, and the ethidium bromide concentration is about 600 $\mu$g/ml. The solution is transferred to a Beckman Type 50 centrifuge tube, filled to the top with paraffin oil, sealed, and centrifuged at 45,000 rpm for 24 hours at 20° C. After centrifugation, two bands of DNA are visible in ordinary light. The cap is removed from the tube, and the lower DNA band is recovered using a syringe with a #21 hypodermic needle inserted through the side of the centrifuge tube.

The ethidium bromide is removed from the solution of plasmid DNA by several extractions with water saturated 1-butanol, and the CsCl is removed by dialysis against TE buffer. After extractions with buffered phenol and then chloroform, the DNA is precipitated, washed with 70% ethanol, and dried. About 1 mg of plasmid pHJL315 DNA was obtained and dissolved in 10 ml of TE buffer.

About 5 $\mu$g of plasmid pHJL315 in 5 $\mu$l of TE buffer were added to 2 $\mu$l of 10X BglII buffer (1.0 M NaCl; 100 mM Tris-HCl, pH=7.4; 100 mM MgCl$_2$; 100 mM 2-mercaptoethanol; and 1 mg/ml BSA), 12 $\mu$l of H$_2$O and 1 $\mu$l (~10 units) of restriction enzyme BglII. The resulting reaction was incubated at 37° C. for 2 hours.

The BglII-digested plasmid pHJL315 DNA was then electrophoresed on a 1% agarose gel until the desired ~5.0 kb BglII restriction fragment was clearly separated from the other digestion products. Visualization of the electrophoresed DNA was accomplished by staining the gel in a dilute solution (0.5 $\mu$g/ml) of ethidium bromide and exposing the stained gel to longwave UV light. After the desired fragment was located, a small slit was made in the gel in front of the fragment, and a small piece of Schleicher and Schuell (Keene, NH 03431) NA-45 DEAE membrane was placed in the slit. Upon further electrophoresis, the ~5.0 kb BglII restriction fragment was non-covalently bound to the DEAE membrane. After the desired fragment was bound to the DEAE membrane, the membrane was removed and rinsed with low salt buffer (100 mM KCl; 0.1 mM EDTA; and 20 mM Tris-HCl, pH=8). Next, the membrane was placed in a small tube and immersed in high salt buffer (1 M NaCl; 0.1 mM EDTA; and 20 mM Tris-HCl, pH=8) and then incubated at 65° C. for one hour to remove the DNA from the DEAE paper. After the 65° C. incubation, the incubation buffer was collected and the membrane rinsed with high salt buffer. The rinse solution was pooled with the incubation buffer before collecting the desired DNA fragments.

The volume of the high salt-DNA solution was adjusted so that the NaCl concentration was 0.25 M, and then three volumes of cold, absolute ethanol were added. The resulting solution was mixed and placed at $-70°$ C. for 10–20 minutes. The solution was chilled and centrifuged at 15,000 rpm for 15 minutes. After another precipitation to remove residual salt, the DNA pellet was rinsed with ethanol, dried, resuspended in 20 $\mu$l of TE buffer, and constituted ~1.0 $\mu$g of the desired ~5.0 kb BglII restriction fragment of plasmid pHJL315. The purified fragment was dissolved in 2 $\mu$l of TE buffer and stored at $-20°$ C.

Plasmid pHJL401 is a Streptomyces cloning vector disclosed and claimed in U.S. patent application Ser. No. 841,920, filed Mar. 20, 1986, incorporated herein by reference. The construction protocol for plasmid pHJL401 is described in Example 14 of Ser. No. 841,920. About 1 $\mu$g of plasmid pHJL401 DNA in one $\mu$l of TE buffer was added to 1 $\mu$l of 10X BamHI buffer (1.5 M NaCl; 60 mM Tris-HCl, pH=7.9; 60 mM MgCl$_2$; and 1 mg/ml BSA), 1 $\mu$l (~10 units) of restriction enzyme BamHI, and 7 $\mu$l of H$_2$O. The resulting reaction was incubated at 37° C. for about 2 hours. Then, 100 $\mu$l of 50 mM Tris-HCl, pH=8 were added to the solution of BamHI-digested plasmid pHJL401 DNA together with 1 $\mu$l of a 1:100 dilution of calf-intestinal alkaline phosphatase (Boehringer-Mannheim Biochemicals, 7941 Castleway Dr., P.O. Box 50816, Indianapolis, Ind. 46250), and the reaction mixture was again placed at 37° C. for 30 minutes.

About 34 $\mu$l of the BamHI-digested, phosphatase treated plasmid pHJL401 DNA were added to 1 $\mu$l of the solution of the ~5.0 kb BglII restriction fragment of plasmid pHJL315. The mixture of DNA was precipitated with NaCl and ethanol as described above, and the pellet was resuspended in 10 $\mu$l of 1X ligase buffer (50 mM Tris-HCl, pH=7.8; 10 mM MgCl$_2$; 5 mM dithiothreitol; 5% glycerol; and 0.15 mM ATP) containing 6 units of T4 DNA ligase (Boehringer-Mannheim). The ligation reaction was incubated at 4° C. overnight (~16 hours) and constituted the desired plasmids pSFH62 and pSFH63. A restriction site and function map of plasmid pSFH62 is presented in FIG. 4 of the accompanying drawings, and plasmid pSFH63 differs from plasmid pSFH62 only with respect to the orientation of the ~5.0 kb BglII restriction fragment. The ligated DNA was used to transform E. coli K12 JM109 in substantial accordance with the procedure described below.

To prepare E. coli K12 JM109 cells that are competent for transformation, the lyophils of E. coli K12 JM109 obtained from the ATCC under the accession number ATCC 53323 are reconstituted to isolate single colonies. One single-colony isolate of JM109 is inoculated into 5 ml of L broth (10 g of Bacto-tryptone, 10 g of NaCl, and 5 g of Bacto-Yeast Extract per liter) that contains 10 mM MgSO$_4$ and 10 mM MgCl$_2$, and the culture is incubated at 37° C. overnight with aeration. Fifty μl of the overnight culture were used to inoculate 5 ml of L broth that contained 10 mM MgSO₄ and 10 mM MgCl₂. The culture was incubated at 37° C. overnight with aeration. The following morning, the culture was diluted to 200 ml with L broth that contained 10 mM MgSO₄ and 10 mM MgCl₂. The diluted culture was incubated at 37° C. with aeration until the absorbance at 550 nm ($A_{550}$) was about 0.5, which indicated a cell density of about $1 \times 10^8$ cells/ml. The culture was cooled for ten minutes in an ice-water bath, and the cells were then collected by centrifugation at 4000Xg for 10 minutes at 4° C. The cell pellet was resuspended in 100 ml of cold 10 mM NaCl and then immediately repelleted by centrifugation. The cell pellet was resuspended in 100 ml of 30 mM CaCl₂ and incubated on ice for 20 minutes.

The cells were again collected by centrifugation and resuspended in 10 ml of 30 mM CaCl₂. A one-half ml aliquot of the cells was added to the ligated DNA prepared above; the DNA had been made 30 mM in CaCl₂. The cell-DNA mixture was incubated on ice for one hour, heat-shocked at 42° C. for 90 seconds, and then chilled on ice for about two minutes. The cell-DNA mixture was diluted into 10 ml of L broth in a 125 ml flask and incubated at 37° C. for one hour.

The BamHI site on plasmid pHJL401 resides within a polylinker that itself forms part of the DNA sequence encoding the lacZ α-fragment. Expression of the lacZ α-fragment in an *E. coli* ΔM15, or similar type, mutant, such as JM109, restores the mutant's ability to produce a functional β-galactosidase enzyme. Thus, plasmid pHJL401 can restore β-galactosidase activity to an *E. coli* ΔM15 mutant. However, insertion of DNA into a restriction site of the polylinker on plasmid pHJL401, as occurs in the construction of plasmid pSFH62, disrupts the lacZ α-fragment coding sequence and concomitantly destroys the ability of the pHJL401 derivative to complement a ΔM15-type mutation. β-galactosidase can hydrolyze X-Gal, which is 5-bromo-4-chloro-3-indolyl-β-D-galactopyranoside, a colorless compound, to an indigo-colored product and thus allows for a convenient screening method for discriminating between transformants containing starting plasmid pHJL401 or modified plasmid, such as pSKC13, pSFH62, and pSFH63. Thus, aliquots of the transformation mixture were plated on L-agar (L-broth with 15 grams per liter agar) plates containing 100 μg ampicillin/ml, 40 μg X-gal/ml, and 40 μg IPTG/ml. IPTG serves to induce the lac promoter present on plasmid pHJL401. The plates were incubated at 37° C. overnight. Colonies that contain a plasmid with an insert, such as *E. coli* K12 JM109/pSFH62, are white. Several ampicillin-resistant, white colonies were selected and then screened by restriction analysis of their plasmid DNA for the presence of the ~5.0 kb BqlII restriction fragment containing tlrB. In this manner, the desired *E. coli* K12 JM109/pSFH62 and *E. coli* K12 JM109/pSFH63 transformants were identified and isolated.

Plasmid pSKC13 was constructed by a procedure similar to that used for plasmids pSFH62 and pSFH63. However, in the construction of plasmid pSKC13, the BglII digestion to isolate the ~5.0 kb tlrB-containing restriction fragment did not go to completion. Instead, the ~0.2 kb BglII restriction fragment adjacent to the ~5.0 kb BglII restriction fragment on plasmid pHJL315 was inserted along with the ~5.0 kb fragment into BamHI-digested plasmid pHJL401 to yield plasmid pSKC13. The ligated DNA was used to transform *E. coli* K12 JM109 in substantial accordance with the procedure described above, and the *E. coli* K12 JM109/pSKC13 transformants were identified by their ampicillin-resistant phenotype and by restriction enzyme analysis of their plasmid DNA. A restriction site and function map of plasmid pSKC13 is presented in FIG. 5 of the accompanying drawings.

EXAMPLE 4

Construction of Plasmids pSFH60, pSFH60.1, and pSFH61

A. Construction of Plasmids pSFH60 and pSFH60.1

About 1 μg of plasmid pUC19 (ATCC 37254) in 1 μl of TE buffer was added to 2 μl of 10X KpnI buffer (60 mM NaCl; 60 mM Tris-HCl, pH=7.5; 60 mM MgCl₂; 10 mM DTT; and 1 mg/ml BSA), 1 μl (~10 units) of restriction enzyme KpnI, and 16 μl of H₂O. The reaction was incubated at 37° C. for 2 hours and terminated by incubation of the reaction mixture at 70° C. for 10 minutes.

About 5 μg of plasmid pSKC13 in 5 μl of TE buffer were added to 2 μl of 10X KpnI buffer, 1 μl (~10 units) of restriction enzyme KpnI, and 12 μl of H₂O, and the resulting reaction was incubated at 37° C. for about 2 hours. The reaction was terminated by incubating the reaction mixture at 70° C. for 10 minutes. The reaction mixture was then loaded onto a 1% agarose gel and subjected to electrophoresis until the ~3.8 kb tlrB-containing restriction fragment was well separated from the other digestion products. About 1 μg of the ~3.8 kb, tlrB-containing KpnI restriction fragment was isolated from the gel and purified in substantial accordance with the procedure of Example 3.

About 0.5 μg of the ~3.8 kb, tlrB-containing KpnI restriction fragment and ~0.1 μg of the KpnI-digested plasmid pUC19 DNA were mixed together, precipitated with ethanol and NaCl, and resuspended in 10 μl of 1X ligase buffer containing ~6 units of T4 DNA ligase (Boehringer-Mannheim). The ligation reaction was incubated at 4° C. overnight (~16 hours); the ligated DNA constituted the desired plasmids pSFH60 and pSFH60.1, which differ from one another only with respect to the orientation of the ~3.8 kb KpnI restriction fragment. A restriction site and function map of plasmid pSFH60 is presented in FIG. 6 of the accompanying drawings.

The ligated DNA was used to transform *E. coli* K12 JM109 in substantial accordance with the procedure of Example 3. Plasmid pUC19, like plasmid pHJL401, encodes the lacZ α-fragment, and the single KpnI site on plasmid pUC19 is located within the lacZ α-fragment-encoding DNA. Consequently, the transformed cells were plated on L agar containing ampicillin, X-Gal, and IPTG. The plasmid DNA of the colorless ("white"), ampicillin-resistant transformants was subjected to restriction enzyme analysis to identify the desired *E. coli* K12 JM109/pSFH60 and *E. coli* K12 JM109/pSFH60.1 transformants. Plasmid pSFH60 DNA was prepared from the *E. coli* K12 JM109/pSFH60 transformants for use in the construction of plasmid pSFH61 in substantial accordance with the procedure described in Example 3.

B. Construction of Plasmid pSFH61.

About 5 μg of plasmid pSFH60 DNA in 5 μl of TE buffer were added to 2 μl of 10X HindIII buffer (0.5 M NaCl; 0.5 M Tris-HCl, pH=8; 0.1 M MgCl₂; and 1 mg/ml BSA), 1 μl (~20 units) of restriction enzyme HindIII, and 12 μl of H₂O, and the resulting reaction was incubated at 37° C. for 2 hours. The HindIII-digested plasmid pSFH60 DNA was then precipitated with ethanol and NaCl and resuspended in 17 μl of H₂O. About 2 μl of 10X EcoRI buffer (1 M Tris-HCl, pH=7.5; 0.5 M NaCl; 50 mM MgCl₂; and 1 mg/ml BSA) and 1 μl (~20 units) of restriction enzyme EcoRI were added to the solution of HindIII-digested plasmid pSFH60 DNA, and the resulting reaction was incubated at 37° C. for two hours. The EcoRI-HindIII-digested plasmid pSFH60 DNA was loaded onto an agarose gel and subjected to electrophoresis until the ~3.8 kb, tlrB-containing restriction fragment was separated from the other digestion products. The ~3.8 kb fragment was isolated from the gel and purified in substantial accordance with the procedure of Example 3; about 1 μg of the fragment was obtained.

About 1 μg of plasmid pHJL401 was digested with restriction enzymes EcoRI and HindIII as described above. The digestions were terminated by incubating the reaction mixture at 70° C. About 0.1 μg of the EcoRI-HindIII-digested plasmid pHJL401 DNA was mixed with about 0.5 μg of the ~3.8 kb EcoRI-HindIII restriction fragment of plasmid pSFH60, and then, the DNA was precipitated with ethanol and NaCl. The DNA was resuspended in 10 μl of 1X ligase buffer containing 6 units of T4 DNA ligase (Boehringer-Mannheim), and the resulting reaction was incubated at 4° C. overnight (~16 hours).

The ligated DNA constituted the desired plasmid pSFH61 and was used to transform *E. coli* K12 JM109 in substantial accordance with the procedure of Example 3. The ampicillin-resistant transformants that failed to hydrolyze X-Gal were subjected to restriction enzyme analysis of their plasmid DNA to identify the desired *E. coli* K12 JM109/pSFH61 transformants. A restriction site and function map of plasmid pSFH61 is presented in FIG. 7 of the accompanying drawings.

EXAMPLE 5

Construction of Plasmids pSVB36 and pSVB37

Figure 9:
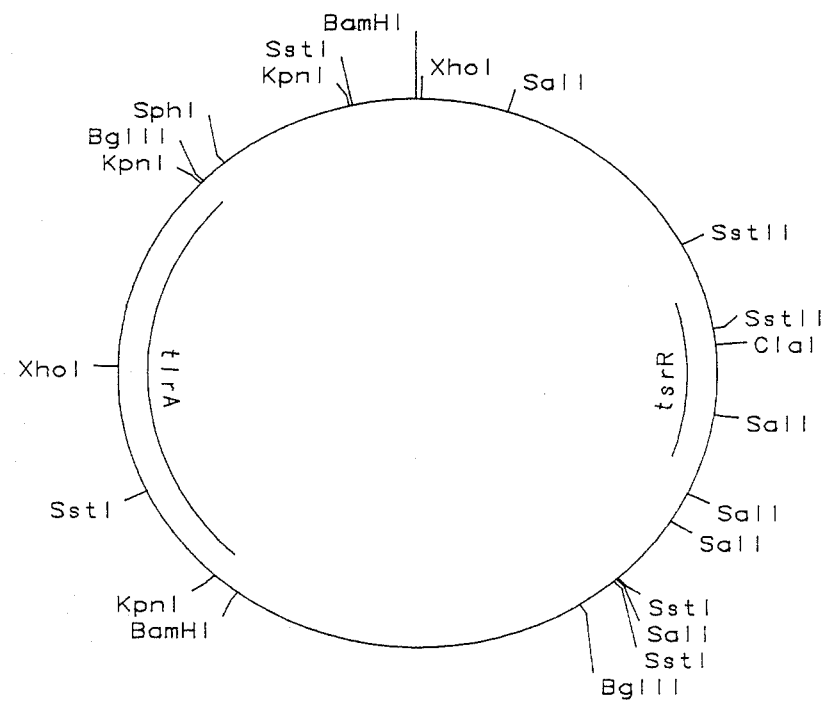
FIG. 9 is a restriction site and function map of plasmid pSVB2.
Figure 10:
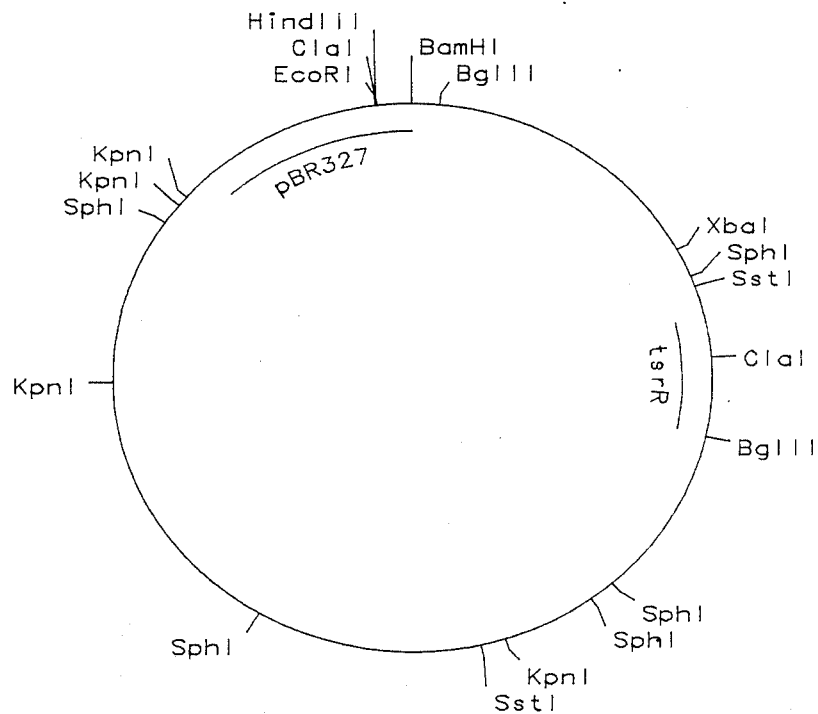
FIG. 10 is a restriction site and function map of plasmid pIJ903.

*Streptomyces lividans* TK23/pSVB2 (NRRL 15880) was cultured and treated in substantial accordance with the procedure of Example 1 to isolate plasmid pSVB2 DNA. A restriction site and function map of plasmid pSVB2 is presented in FIG. 9 of the accompanying drawings. About 500 ng of plasmid pSVB2 DNA in 5 μl of TE buffer were added to 12 μl of H₂O, 2 μl of 10X ClaI buffer (0.5 M NaCl; 60 mM Tris-HCl, pH=7.9; 60 mM MgCl₂; and 1 mg/ml BSA), and 2 μl (~14 units) of restriction enzyme ClaI, and the resulting reaction was incubated at 37° for one hour. The ClaI digestion reduces undesired ligation products in the ligation to produce plasmids pSVB36 and pSVB37.

About 1 μl of 1 M NaCl and 1 μl (~8 units) of restriction enzyme BglII were added to the solution of ClaI-digested plasmid pSVB2 DNA, and the reaction was incubated at 37° C. for another hour. About 5 μl of the reaction mixture were removed and subjected to agarose gel electrophoresis to determine completeness of digestion. About 4 μl of 10X BamHI buffer (1.5 M NaCl; 60 mM Tris-HCl, pH=7.9; 60 mM MgCl₂; and 1 mg/ml BSA), 19 μl of H₂O, and 2 μl (~48 units) of restriction enzyme BamHI were added to the remaining ~17 μl of BglII-ClaI-digested plasmid pSVB2 DNA, and the reaction mixture was incubated at 37° C. for one hour.

About 500 ng of plasmid pSVB25 DNA (prepared from *Streptomyces lividan* TK23/pSVB25 cells in substantial accordance with the procedure described in Example 1, above) in 5 μl of TE buffer were added to 11 μl of H₂O, 2 μl of 10X BglII buffer, and 2 μl (~16 units) of restriction enzyme BglII, and the resulting reaction was incubated at 37° C. for one hour. About 5 μl of the reaction mixture were subjected to agarose gel electrophoresis to determine the completeness of the BglII digestion, and the remaining BglII-digested plasmid pSVB25 DNA was precipitated with ethanol and treated with calf-intestinal alkaline phosphatase in substantial accordance with the procedure of Example 2.

About 25 μl of the ClaI-BglII-BamHI-digested plasmid pSVB2 DNA and about 67 μl of the BglII-digested, alkaline phosphatase-treated plasmid pSVB25 DNA were mixed together with 9.2 μl of 3 M NaOAc and 250 μl of ethanol. The mixture was chilled at −70° C. for 30 minutes and then centrifuged to pellet the DNA. The pellet was resuspended in 10 μl of 1X ligase buffer that contained 1 unit of T4 DNA ligase, and the resulting reaction was incubated at 15° C. overnight. The ligated DNA constituted the desired plasmids pSVB36 and pSVB37. A restriction site and function map of plasmid pSVB36 is presented in FIG. 8 of the accompanying drawings. About 5 μl of the ligated DNA were used to transform *Streptomyces lividans* TK23, as described in Example 6. The desired *S. lividans* TK23/pSVB36 and *S. lividans* TK23/pSVB37 transformants were identified by their tylosin-resistant phenotype and by restriction enzyme analysis of their plasmid DNA.

EXAMPLE 6

Construction of Tylosin-Resistant *Streptomyces lividans* TK23 Transformants

A. List of Solutions

The following solutions are referred to throughout the Examples and are presented here for clarity.

1. P medium (~100 ml):

| Ingredient | Amount |
|---|---|
| Sucrose | 10.3 g |
| K₂SO₄ | 0.025 g |
| Trace element solution (see #3) | 0.2 ml |
| MgCl₂.6H₂O | 0.203 g |
| Water | 80 ml |
| After autoclaving add: | |
| KH₂PO₄ (0.5%) | 1 ml |
| CaCl₂.2H₂O (3.68%) | 10 ml |
| (N—tris-(hydroxymethyl)-methyl-2-aminoethane sulphonic acid), "TES" buffer, 0.25 M, pH = 7.2 | 10 ml |

2. L medium (~100 ml):

| Ingredient | Amount |
|---|---|
| Sucrose (10.3%) | 100 ml |
| TES buffer, pH 7.2 (0.25 M) | 10 ml |
| K₂SO₄ (2.5%) | 1 ml |
| Trace element solution (see #3) | 0.2 ml |
| KH₂PO₄ (0.5%) | 1 ml |

| Ingredient | Amount |
| --- | --- |
| MgCl$_2$ (2.5 M) | 0.1 ml |
| CaCl$_2$ (0.25 M) | 1 ml |
| Lysozyme | 1 mg/ml |

The L medium is filter sterilized after preparation.

3. Trace element solution (~1 l):

| Ingredient | Amount |
| --- | --- |
| ZnCl$_2$ | 40 mg |
| FeCl$_3$.6H$_2$O | 200 mg |
| CuCl$_2$.2H$_2$O | 10 mg |
| MnCl$_2$.4H$_2$O | 10 mg |
| Na$_2$B$_4$O$_7$.10H$_2$O | 10 mg |
| (NH$_4$)$_6$Mo$_7$O$_{24}$.4H$_2$O | 10 mg |
| H$_2$O | 1 l |

4. R2 Regeneration Medium (~1 l):

| Ingredient | Amount |
| --- | --- |
| Sucrose | 103 g |
| K$_2$SO$_4$ | 0.25 g |
| Trace element solution | 2 ml |
| MgCl$_2$.6H$_2$O | 10.12 g |
| glucose | 10 g |
| L-asparagine.1H$_2$O | 2.0 g |
| casamino acids | 0.1 g |
| Agar | 22 g |
| Water to | 700 ml |
| After autoclaving add: | |
| KH$_2$PO$_4$ (0.05 g/100 ml) | 100 ml |
| CaCl$_2$ (2.22 g/100 ml) | 100 ml |
| TES Buffer (5.73 g/100 ml, pH = 7.2) | 100 ml |
| NaOH (5 N) | 1 ml |

5. T medium (~14.5 ml):

| Ingredient | Amount |
| --- | --- |
| Sucrose (10.3%) | 2.5 ml |
| Distilled water | 7.5 ml |
| Trace element solution | 20 μl |
| K$_2$SO$_4$ (2.5%) | 100 μl |
| CaCl$_2$ (5 M) | 217 μl |
| Tris-maleic acid, pH = 8 (1 M) | 543 μl |
| Polyethylene glycol 1000 | 3.63 g |

All components were stabilized before use. The liquid components were mixed and then added to the appropriate amount of molten polyethylene glycol. The first four ingredients may be pre-mixed and stored at room temperature for at least one month.

6. Soft nutrient agar (SNR, ~1 l):

| Ingredient | Amount |
| --- | --- |
| Difco Bacto Nutrient Broth | 8 g |
| Agar | 5 g |

7. R2YE medium is R2 medium with 20 ml of 25% yeast extract added per liter.

8. Yeast Extract - Malt Extract (YEME, ~1 l):

| Ingredient | Amount |
| --- | --- |
| Yeast extract | 3 g |
| Peptone | 5 g |
| Malt extract | 3 g |
| Glucose | 10 g |

9. YEME +34% Sucrose Liquid Completer Medium is YEME with 340 g/liter of sucrose.

10. YMX Media (~1 l):

| Ingredient | Amount |
| --- | --- |
| Yeast extract | 3 g |
| Malt extract | 3 g |
| Glucose | 2 g |
| Agar | 20 g |

B. Preparation and Storage of Protoplasts

The procedure described in this Example was con- struct and analyze *Streptomyces lividans* TK23 transformants. Plasmids pSVB9, pSVB25, pSVB36, pSVB37, pSFH61, pSVB47, pSFH62, pSFH63, and pSKC13 were each separately and independently used as the transforming DNA.

*Streptomyces lividans* TK23 (NRRL 15826) were grown for 40–48 hours at 30° C. in YEME+34% sucrose, 5 mM MgCl$_2$, and 0.5% glycine. The mycelium was recovered by centrifugation (800Xg for 10 minutes in a bench top centrifuge) and washed twice in 10.3% sucrose. The mycelium from 25–50 ml of culture was suspended in 3–4 ml of L medium and incubated for 1 hour at 32° C.. During this interval the suspension was pipetted up and down once or twice to disperse clumps. Five ml of P medium were added, and the suspension was then filtered through a plug of cotton wool. The protoplasts were recovered by centrifugation (800Xg for 10 minutes) and washed twice with 5 ml of P medium. The protoplasts were then suspended in 4 ml of P medium and the number of protoplasts determined microscopically using a hemacytometer slide. If the protoplasts are not to be used immediately, the suspension can be divided into aliquots (about 1 ml) containing $5 \times 10^9$–$10^{10}$ protoplasts in sterile polypropylene screw-cap tubes. The suspensions were frozen slowly by placing the tubes in a container of ice, which was in turn placed at −70° C. The protoplasts were stored at this temperature until needed. The frozen suspension was thawed rapidly by immersion in a 37° C. water bath prior to use.

C. Protoplast Transformation

Approximately $5 \times 10^9$ protoplasts were pelleted by centrifugation (800Xg for 10 minutes). The supernatant was decanted and the protoplasts were resuspended in the small volume of liquid remaining in the tube. Plasmid DNA in a volume not greater than 20 μl in TE buffer was added, followed immediately by the addition of 0.5 ml of T medium. The mixture was pipetted up and down once or twice to mix the contents. At this point the suspension was either plated directly or diluted with 0.5 ml of P medium and then plated. In either case, about 0.1 ml was inoculated per plate of R2YE medium.

Tylosin-resistant transformants were selected by replica-plating regenerated protoplasts to R2YE medium containing 500 μg/ml of tylosin. Alternatively, tylosin-resistant transformants can be selected by overlaying the regenerating protoplasts with soft nutrient broth agar containing tylosin. The regeneration plates are incubated for 16–22 hours at 30° C. before the application of 2.5 ml per plate of SNA (at a temperature of 45°–50° C.) containing enough tylosin to give a final concentration of 500 μg/ml after diffusion. Melanin production, or lack thereof, by transformants carrying pIJ702 derivatives was detected by incorporating tyrosine at 750 μg/ml into the SNA overlay; those transformants possessing an intact tyrosinase gene become black after growth in the presence of tyrosine.

D. Analysis of *Streptomyces lividans* Transformants

The transformants are cultured on R2YE agar supplemented with tylosin (500 μg/ml) to obtain single colonies. These single colonies are used to inoculate 10 ml TSB cultures also containing thiostrepton (20 μg/ml). The cultures are homogenized and then grown overnight at 30° C. in a rotary shaker.

Plasmid isolation for analysis is done by a small-scale version of the protocol of Example 1; the CsCl gradients of Example 1 are replaced by ethanol precipitations. The mycelium is collected by centrifugation, washed twice with 10.3% sucrose and then suspended in 1–2 ml of 10.3% sucrose. Four hundred μl of the cell mixture are transferred to a small tube, and 100 μl of 5X Lysozyme solution (Example 1) are added. The suspension is incubated at 30° C. for 30–60 minutes, followed by the addition and mixing of 300 μl of 0.3 M NaOH containing 1% SDS. The latter solution is kept at 50° C. before its addition to the cell mix. The cell mixture is placed at 80° C. for 10 minutes, cooled to room temperature, and then extracted with 200 μl of phenol:CHCl$_3$ (50:50). The aqueous phase is transferred to a clean tube, made 0.3 M in NaOAc, and then one volume of isopropanol is added. The DNA is incubated at room temperature for five minutes and then pelleted by centrifugation. The pellet is dissolved in 400 μl of TE buffer and made 0.3 M in NaOAc. About 2.5 volumes of ethanol are added, and the mixture is incubated at −70° C. for 30 minutes. After centrifugation and another precipitation, the plasmid DNA is suspended in 50 μl of TE buffer. Restriction enzyme cutting and electrophoretic analysis of the reaction products are used to determine plasmid structure.

EXAMPLE 7

Construction of Plasmid pSVB47

A. Construction of Plasmid pSVB40

About 1.2 μg of plasmid pUC19 DNA in 4 μl of TE buffer were added to 2 μl of 10X SacI buffer (60 mM Tris-HCl, pH=7.4; 60 mM MgCl$_2$; 60 mM 2-mercaptoethanol; and 100 mg/ml BSA), 1 μl (~10 units) of restriction enzyme SacI, and 13 μl of H$_2$O. The resulting reaction was incubated at 37° C. for 1 hour. About 6 μl of 10X BglII buffer, 2 μ(~20 units) of restriction enzyme BglII, and 32 μl of H$_2$O were added to the solution of SacI-digested plasmid pUC19 DNA, and the reaction was placed at 37° C. for another hour.

About 1 μg of plasmid pSVB25 DNA in 10 μl of TE buffer were added to 2 μl of 10X SacI buffer, 1 μl (~10 units) of restriction enzyme SacI, and 7 μl of H$_2$O, and the resulting reaction was incubated at 37° C. for 1 hour. About 6 μl of 10X BglII buffer, 2 μl (~20 units) of restriction enzyme BglII, and 32 μl of H$_2$O were added to the solution of SacI-digested plasmid pSVB25 DNA, and the resulting reaction was incubated at 37° C. for 1 hour.

About 150 ng (~7.5 μl) of SacI-BglII-digested plasmid pUC19 and 375 ng (~22 μl) of SacI-BglII-digested plasmid pSVB25 were mixed together and precipitated with NaCl and ethanol. The DNA was resuspended in 5 μl of 1X ligase buffer containing 3 units of T4 DNA ligase (Boehringer-Mannheim), and the resulting reaction was incubated at 4° C. for about 66 hours. The ligated DNA constituted the desired plasmid pSVB40; a restriction site and function map of plasmid pSVB40 is presented in FIG. 11 of the accompanying drawings. The ligated DNA was used to transform *E. coli* K12 JM109 in substantial accordance with the procedure of Example 3. The transformed cells were plated on L agar containing 40 μg/ml IPTG, 40 μg/ml X-Gal, and 100 μg/ml ampicillin. Non-indigo-colored colonies were screened by restriction enzyme analysis to identify the desired *E. coli* K12 JM109/pSVB40 transformants. Plasmid DNA was obtained from the *E. coli* K12 JM109/pSVB40 transformants for use in the construction of plasmid pSVB47 in substantial accordance with the procedure described in Example 3.

B. Construction of Plasmid pSVB47

About 1.2 μg of plasmid pIJ903 DNA in 4 μl of TE buffer were added to 2 μl of 10X HindIII buffer, 1 μl (~10 units) of restriction enzyme HindIII, and 13 μl of H$_2$O. The resulting reaction was incubated at 37° C. for 1 hour. About 6 μl of 10X EcoRI buffer, 2 μl (~20 units) of restriction enzyme EcoRI, and 32 μl of H$_2$O were added to the solution of HindIII-digested plasmid pIJ903 DNA, and the reaction was placed at 37° C. for another hour.

About 1 μg of plasmid pSVB40 DNA in 10 μl of TE buffer was added to 2 μl of 10X HindIII buffer, 1 μl (~10 units) of restriction enzyme HindIII, and 7 μl of H$_2$O, and the resulting reaction was incubated at 37° C. for 1 hour. About 6 μl of 10X EcoRI buffer, 2 μl (~20 units) of restriction enzyme EcoRI, and 32 μl of H$_2$O were added to the solution of HindIII-digested plasmid pSVB40 DNA, and the resulting reaction was incubated at 37° C. for 1 hour.

About 150 ng (~7.5 μl) of HindIII-EcoRI-digested plasmid pIJ903 and 375 ng (~22 μl) of HindIII-EcoRI-digested plasmid pSVB40 were mixed together and precipitated with NaCl ad ethanol. The DNA was resuspended in 5 μl of 1X ligase buffer containing 3 units of T4 DNA ligase (Boehringer-Mannheim). The ligated DNA constituted the desired plasmid pSVB47; a restriction site and function map of plasmid pSVB47 is presented in FIG. 12 of the accompanying drawings. The ligated DNA was used to transform *Streptomyces lividans* in substantial accordance with the procedure of Example 6.

We claim:
1. The insulated tlrB gene of *Streptomyces fradiae*.
2. A recombinant DNA construct comprising the tlrB gene of *Streptomyces fradiae*.
3. The DNA of claim 2 which is the ~3.35 kb SacI-BglII restriction fragment of plasmid pSVB9.
4. The recombinant DNA construct of claim 2 which is a recombinant DNA cloning vector.
5. A recombinant DNA cloning vector of claim 4 that is a plasmid.
6. A plasmid of claim 5 selected from the group consisting of plasmids pSVB9, pSVB25, pSVB36, pSVB37, pSVB40, pSVB47, pSKC13, pSFH60, pSFH60.1, and
7. The plasmid of claim 6 that is plasmid pSVB9.
8. The plasmid of claim 6 that is plasmid pSVB25.
9. The plasmid of claim 6 that is plasmid pSVB36.

10. The plasmid of claim 6 that is plasmid pSVB47.
11. The plasmid of claim 6 that is plasmid pSKC13.
12. The plasmid of claim 6 that is plasmid pDGH60.
13. The plasmid of claim 6 that is plasmid pSFH61.
14. A host cell transformed with a recombinant DNA cloning vector of claim 4.
15. A host cell transformed with a plasmid of claim 5.
16. The host cell of claim 15 that is Streptomyces.
17. The host cell of claim 16 that is selected from the group consisting of *Streptomyces fradiae* and *Streptomyces lividans*.
18. The host cell of claim 17 that is *S. lividans*/pSVB9.
19. The host cell of claim 17 that is *S. lividans*/pSVB25.
20. The host cell of claim 17 that is *S. lividans*/pSVB36.
21. The host cell of claim 17 that is *S. lividans*/pSVB47.
22. The host cell of claim 17 that is *S. lividans*/pSKC13.

* * * * *

UNITED STATES PATENT AND TRADEMARK OFFICE
CERTIFICATE OF CORRECTION

PATENT NO. : 4,879,241

DATED : November 7, 1989

INVENTOR(S) : Virginia A. Birmingham and Eugene T. Seno

It is certified that error appears in the above-identified patent and that said Letters Patent is hereby corrected as shown below:

In Claim 1, line 1, "insulated" should read --isolated--.

In Claim 6, line 3, after "and" add --pSFH61--.

In Claim 12, line 1, "pDGH60" should read --pSFH60--.

Signed and Sealed this

Second Day of October, 1990

Attest:

HARRY F. MANBECK, JR.

Attesting Officer

Commissioner of Patents and Trademarks